United States Patent
Potet et al.

(10) Patent No.: US 10,702,720 B2
(45) Date of Patent: Jul. 7, 2020

(54) ASSEMBLY COMPRISING A RESPIRATORY MASK AND A STOWAGE DEVICE, METHOD FOR STOWING A RESPIRATORY MASK AND METHOD FOR PROVIDING A RESPIRATORY MASK

(71) Applicant: Zodiac Aerotechnics, Plaisir (FR)

(72) Inventors: Olivier Potet, La Ville-du-Bois (FR); Jean-Baptiste Delprat, Chaville (FR)

(73) Assignee: Zodiac Aerotechnics, Plaisir (FR)

( * ) Notice: Subject to any disclaimer, the term of this patent is extended or adjusted under 35 U.S.C. 154(b) by 215 days.

(21) Appl. No.: 16/027,661

(22) Filed: Jul. 5, 2018

(65) Prior Publication Data
US 2019/0009116 A1    Jan. 10, 2019

Related U.S. Application Data

(60) Provisional application No. 62/528,760, filed on Jul. 5, 2017.

(51) Int. Cl.
| | | |
|---|---|---|
| *A62B 9/04* | (2006.01) | |
| *A62B 7/14* | (2006.01) | |
| *B64D 10/00* | (2006.01) | |
| *A62B 25/00* | (2006.01) | |
| *A62B 18/08* | (2006.01) | |
| *A61F 9/02* | (2006.01) | |

(52) U.S. Cl.
CPC .................. *A62B 9/04* (2013.01); *A62B 7/14* (2013.01); *A62B 18/084* (2013.01); *A62B 25/005* (2013.01); *B64D 10/00* (2013.01); *A61F 9/02* (2013.01); *B64D 2231/025* (2013.01)

(58) Field of Classification Search
CPC ......... A61B 7/14; A61B 18/02; A61B 18/084; A61B 25/005; B64D 11/0689; B64D 25/00
See application file for complete search history.

(56) References Cited

U.S. PATENT DOCUMENTS

| | | | | |
|---|---|---|---|---|
| 2002/0189617 | A1* | 12/2002 | Cordero ............... | A62B 25/005 128/205.25 |
| 2003/0188989 | A1* | 10/2003 | Taieb ................... | A62B 25/005 206/527 |
| 2004/0144384 | A1* | 7/2004 | Martinez .............. | A62B 25/005 128/204.29 |

FOREIGN PATENT DOCUMENTS

WO    2017/055764 A1    4/2017

* cited by examiner

*Primary Examiner* — Justin M Benedik
(74) *Attorney, Agent, or Firm* — Kilpatrick Townsend & Stockton LLP; Dean W. Russell

(57) ABSTRACT

Assembly intended in particular to be arranged in a cockpit of an aircraft, said assembly comprising a respiratory mask and a stowage device, wherein:
 the respiratory mask has a face cover and a harness,
 the stowage device comprises a base and a platform,
 the platform is adapted to receive the respiratory mask in a stowage position where the harness forms a loop extending around the platform,
 the platform comprises a main element movable relative to the base between a retracted position and a protruding position, and
 the platform further comprises auxiliary elements, the auxiliary elements movable with respect to the main element between a flattened configuration and an expanded configuration of the platform.

19 Claims, 7 Drawing Sheets

ASSEMBLY COMPRISING A RESPIRATORY MASK AND A STOWAGE DEVICE, METHOD FOR STOWING A RESPIRATORY MASK AND METHOD FOR PROVIDING A RESPIRATORY MASK

CROSS-REFERENCE TO RELATED APPLICATIONS

This application is related to and claims the benefit of U.S. Provisional Application No. 62/528,760 ("the '760 application"), filed on Jul. 5, 2017, entitled RESPIRATORY MASK CONCEPTS. The '760 application is hereby incorporated in its entirety by this reference.

FUNDING STATEMENT

The project leading to this application has received funding from the Clean Sky 2 Joint Undertaking under the European Union's Horizon 2020 research and innovation program under grant agreement No. CS2-LPA-GAM-2014-2015-0I.

FIELD OF THE DISCLOSURE

The invention relates to an assembly intended in particular to be arranged in a cockpit of an aircraft having a pressurized cabin in order to supply a breathing gas to a crew member. The invention also relates to a method for stowing a respiratory mask and a method for providing a respiratory mask.

BACKGROUND OF THE DISCLOSURE

The invention aims to provide an assembly enabling to stow a respiratory mask and to provide the respiratory mask supplying a breathing gas to a crew member in the event of an emergency for example.

The respiratory mask has a face cover and a harness. The face cover has a respiratory cavity and the harness is extendable between a deflated configuration and an inflated configuration. The respiratory mask is adapted to be placed in a use position in which the facer cover applies on the face of crew member around the mouth and nose. In the use position, the harness is in the (at least partially) deflated configuration and forms a loop extending around the head of the crew member on a side opposite from the face cover so as to hold the face cover on the face of the crew member.

The respiratory mask may further comprise a shield. The shield protects the eyes of the user from any airborne elements, particularly smoke. The shield may also support a display device. The shield may be comprised in the face cover or can be part of separate element which can be released from the face cover.

The assembly comprises the respiratory mask and a stowage device. The respiratory mask may be arranged in a stowage position in the stowage device located in the cabin of a commercial aircraft transporting the crew members and the passengers. The aircraft further comprises a pressurizing device which pressurizes the cabin to enable the passengers and crew members to breathe normally within the cabin.

In case of depressurization, the user of the assembly which is usually the pilot or co-pilot, grabs the respiratory mask which is located in the stowage device. The user then inflates the harness in order to form a large loop through which the head of the user can be put. The respiratory mask is placed around the user's head in order to breathe through the face cover, which thus supplies the user with breathing gas (usually a respiratory gas comprising breathing and ambient gas).

A stowage device for the respiratory mask is therefore important, in order to protect the respiratory mask when not in use.

When an emergency condition is detected, the user has less than five seconds to grab the respiratory mask and position the face cover on his face. Therefore, such a stowage device must also be placed in a predefined position proximate the user, to allow a crew member to quickly grasp the mask and position it on his face.

This is the reason why the stowage devices are sometimes placed in the dashboard of the cockpit, within the reach of the pilot or co-pilot. With the same reasoning, the stowage devices may be located up above, near the pilot or co-pilot.

Document WO2017/055764A1 provides an assembly comprising a respiratory mask having an oronasal face cover and a harness, the oronasal face cover having a respiratory cavity and being suitable for applying on the face of the crew member around the mouth and nose, the harness forming a loop adapted to extend around the head of the user on a side opposite from the oronasal face cover so as to hold the oronasal face cover on the face of the user, and a storage device, said storage device comprising a base and a platform, the platform being mounted so as to be movable relative to the base between a retracted position and an extended position, the platform having a receiving surface, the receiving surface of the platform being adapted to receive the respiratory mask in a storage position where the harness holds the oronasal face cover against the receiving surface of the platform by encircling the platform to form a loop extending around the platform on the opposite side from the oronasal face cover, the respiratory mask being releasable from the storage device.

The assembly disclosed in document WO2017/055764A1 can be placed in most of the aircraft cockpits, as the base can be a bit distant from the user while it is quite easy to use as the platform has a shape close to a head (where the users have habit to place it).

SUMMARY OF THE DISCLOSURE

The assembly disclosed in document WO2017/055764A1 is satisfying, but the present invention aims to reduce the constraint involved by the presence of such an assembly in the design of a cockpit while having an assembly easy to use. For this purpose, according to the invention the assembly has the following features:
  the platform has a front side and a back side,
  the platform has a receiving surface extending around the platform, the receiving surface has a first portion on the front side and a second portion on the back side,
  the platform is adapted to receive the respiratory mask in a stowage position where the harness forms a loop extending around the platform and contacting the receiving surface, the face cover contacting the first portion of the receiving surface and the harness contacting the second portion of the receiving surface, so as to hold the respiratory mask on the platform,
  the platform comprises a main element, the main element being movable relative to the base between a retracted position and a protruding position,
  the platform further comprises auxiliary elements, the auxiliary elements being movable with respect to the main element between a flattened configuration and an expanded configuration of the platform, in the expanded configuration of the platform, the second portion of the receiving surface is at a first longitudinal distance from the first portion of the receiving surface in a longitudinal direction, and in the flattened configuration of the platform, the second portion of the receiving surface is at a second longitudinal distance from the first portion of the receiving surface, the second longitudinal distance being lower than the first longitudinal distance.

Therefore, the size of the base can be smaller which ease the design of cockpit and enables to place the assembly in more numerous existing cockpits or closer to the pilot, without detrimental consequences in the use of the respiratory mask.

According to an advantageous aspect in accordance with the invention, the assembly preferably has the following supplemental features:

the receiving surface further comprises a third portion and a fourth portion, the harness contacts the third portion and the fourth portion of the receiving surface when the respiratory mask is in the stowage position and the platform is in the flattened configuration, the fourth portion of the receiving surface is at a first transverse distance from the third portion of the receiving surface in a transverse direction in the expanded configuration of the platform, the transverse direction being perpendicular to the longitudinal direction, and the fourth portion of the receiving surface is at a second lateral transverse distance from the third portion of the receiving surface in the flattened configuration of the platform, the second transverse distance being higher than the first transverse distance.

Therefore, the circumference of the receiving surface can be substantially the same in the expanded configuration and in the flattened configuration of the platform, so that the respiratory mask is conveniently hold on the platform in the expanded configuration and in the flattened configuration of the platform.

According to a supplementary aspect in accordance with the invention, the second lateral transverse distance is preferably at least 30% higher, more preferably at least 40% higher than the first lateral transverse distance.

According to a supplementary aspect in accordance with the invention, the assembly preferably has the following features:

the respiratory mask has a rigid support supporting the face cover, the harness has a first end connected to the rigid support and a second end connected to the rigid support, in the flattened configuration, along the longitudinal direction, the third portion is between the first end of the harness and the first portion of the receiving surface, and in the flattened configuration, along the longitudinal direction, the fourth portion is between the second end of the harness and the first portion of the receiving surface.

Therefore, the second longitudinal distance can be further reduced.

According to another aspect in accordance with the invention, the assembly has preferably the following features:

the loop of the harness comprises at least one elastic tubular portion and has a first circumferential length in the expanded configuration of the platform and a second circumferential length in the flattened configuration of the platform, and the second circumferential length differs from the first circumferential length variation by less than 25%, preferably less than 10%.

The face cover of the respiratory mask contacts the first portion and is pressed against the first portion of the receiving surface due to the elasticity of the tubular portion of the harness both in the expanded configuration and in the flattened configuration (and preferably between the expanded configuration and the flattened configuration) in order to maintain the respiratory mask on the platform in the stowage position. The lower the variations in the circumferential length of the loop are the lower the variations of the pressure of the harness and the face cover against the receiving surface are, and consequently the lower the maximum pressure exerted by the harness and the face cover against the receiving surface can be while having the respiratory mask safely maintained on the platform.

According to another aspect in accordance with the invention, the platform is preferably urged into the expanded configuration.

Therefore, the platform can be automatically in the expanded configuration when the main member is in the protruding position.

According to a supplementary aspect in accordance with the invention, when the main element is in the retracted position, the platform preferably abuts against an abutment surface of the base maintaining the platform in the flattened configuration.

Therefore, the platform can be automatically in the flattened configuration when the main member is in the retracted position.

According to a supplementary aspect, preferably at least one spring urges the platform into the expanded configuration, and the abutment of the platform against the abutment surface of the base maintains the platform in the flattened configuration when the main element is in the retracted position.

Such a structure is simple and reliable.

According to another aspect in accordance with the invention, the platform preferably comprises:

a first auxiliary element rotatably connected to the main element, a second auxiliary element rotatably connected to the first auxiliary element, a third auxiliary element rotatably connected to the second auxiliary element, and a fourth auxiliary element rotatably connected to the third auxiliary element and to the main element.

According to another aspect in accordance with the invention, the assembly preferably has the following features:

the respiratory mask and the platform have a first overall longitudinal dimension along the longitudinal direction when the platform is in the expanded configuration, the respiratory mask and the platform have a second overall longitudinal dimension along the longitudinal direction when the platform is in the flattened configuration, and the second overall longitudinal dimension is lower than 75%, preferably lower than 65%, of the first overall longitudinal dimension.

In advantageous embodiments, the breathing assembly preferably further has one or more of the following features:

the main element includes the first portion of the receiving surface;

the main element comprises a lever rotatably mounted on the base;

the first auxiliary element, the second auxiliary element, the third auxiliary element and the fourth auxiliary element are rigid;

the second longitudinal distance is lower than 70%, preferably lower than 50% of the first longitudinal distance;

the platform has an overall transverse dimension along a transverse direction in the expanded configuration, the difference between the first longitudinal distance and the overall transverse dimension is lower than 20% of the first longitudinal dimension.

The invention also relates to a method for stowing a respiratory mask wherein an assembly comprising the respiratory mask is intended to be arranged in particular in a cockpit of an aircraft having a pressurized cabin in order to supply breathing gas to a crew member, the respiratory mask having a face cover and a harness, said assembly further comprising a stowage device, the stowage device comprising a base and a platform, the platform comprises a main element movable relative to the base between a retracted position and a protruding position, the platform has a flattened configuration and an expanded configuration. According to the invention, the method for stowing a respiratory mask comprises:

a) placing the main element in the protruding position and the platform in the expanded configuration, the platform having a first longitudinal dimension along a longitudinal direction in the expanded configuration, b) bringing the respiratory mask to a stowage position where the harness forms a loop extending around the platform so as to hold the respiratory mask on the platform, c) moving the main element into the retracted position and placing the platform in the flattened configuration, the platform having a second longitudinal dimension along the longitudinal direction in the flattened configuration, the second longitudinal dimension being smaller than the first longitudinal dimension.

The invention also relates to a method for providing a respiratory mask wherein an assembly comprising the respiratory mask is intended to be arranged in particular in a cockpit of an aircraft having a pressurized cabin in order to supply breathing gas to a crew member, the respiratory mask having a face cover and a harness, said assembly further comprising a stowage device, the stowage device comprising a base and a platform, the platform comprises a main element movable relative to the base between a retracted position and a protruding position, the platform has a flattened configuration and an expanded configuration. According to the invention, the method for providing a respiratory mask comprises:

a) placing the main element in the retracted position, placing the platform in the flattened configuration and placing the respiratory mask in a stowage position where the harness forms a loop extending around the platform so as to hold the respiratory mask on the platform, the platform having a first longitudinal dimension along a longitudinal direction in the expanded configuration and a second longitudinal dimension along the longitudinal direction in the flattened configuration, the second longitudinal dimension being smaller than the first longitudinal dimension, b) moving the main element into the protruding position and placing the platform in the expanded configuration, and c) removing the respiratory mask from the platform.

BRIEF DESCRIPTION OF THE DRAWINGS

Other features and advantages of the present invention will appear in the following detailed description, with reference to the appended drawings in which.

DETAILED DESCRIPTION OF THE DISCLOSURE

Figure 1:
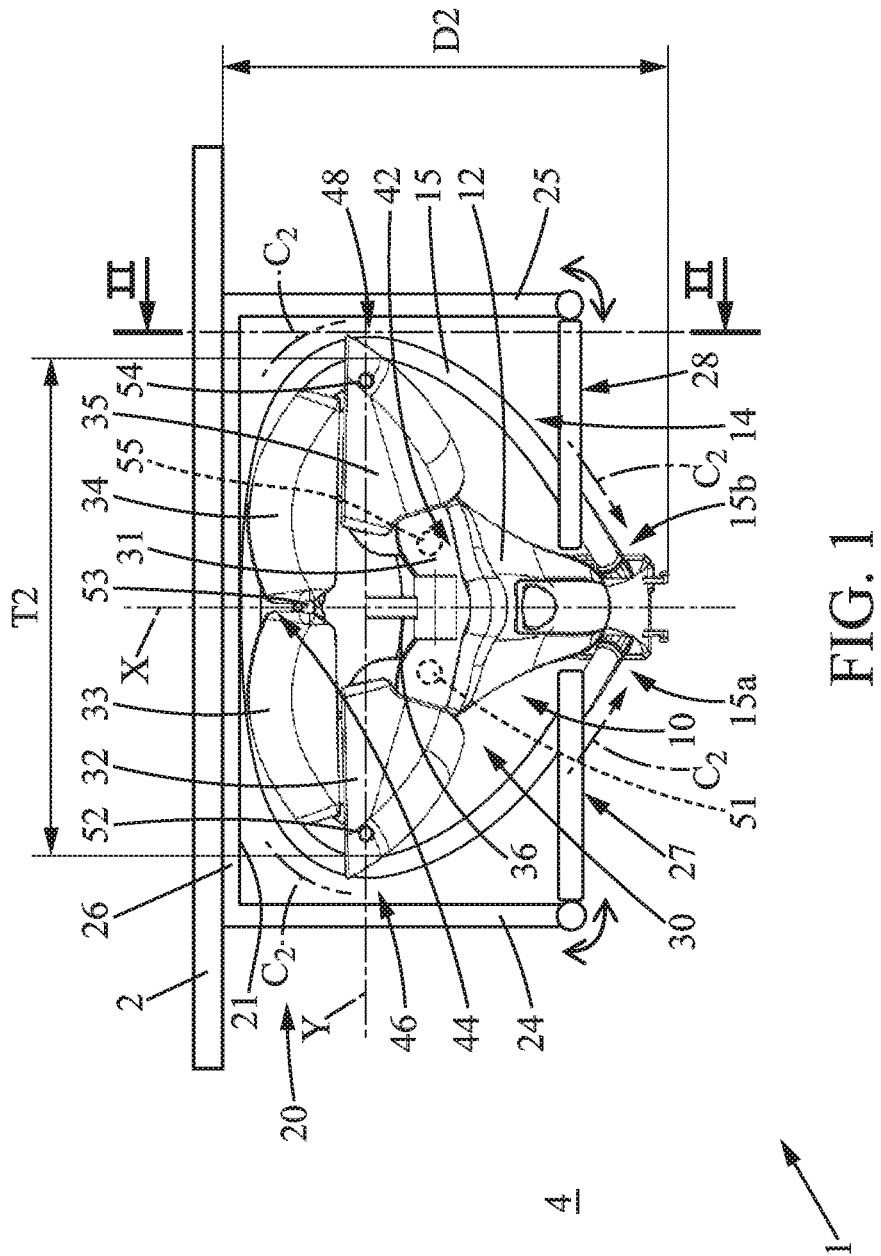
FIG. 1 schematically illustrates a first embodiment of assembly according to the invention comprising a respiratory mask and a platform, the assembly is shown along line referenced I-I in FIG. 2, the platform being in a flattened configuration, FIG. 2 schematically illustrates the assembly shown along line referenced II-II in FIG. 1, FIG. 3 schematically illustrates the assembly, in accordance with FIG. 1, in an intermediate configuration of the platform, FIG. 4 partially illustrates the assembly, in accordance with FIG. 1, in an expanded configuration of the platform, FIG. 5 partially illustrates the assembly, in perspective, in the expanded configuration of the platform, the respiratory mask being released from the platform, FIG. 6 partially illustrates a second embodiment of assembly according to the invention, in perspective, the platform being in the flattened configuration, FIG. 7 partially illustrates the second embodiment of assembly, shown along arrow referenced VII in FIG. 6, FIG. 8 partially illustrates the second embodiment of assembly, in perspective, in accordance with FIG. 6, the platform being in the expanded configuration, FIG. 9 partially illustrates the second embodiment of assembly, in accordance with FIG. 7, the platform being in the expanded configuration.

FIGS. 1 to 5 illustrate a first embodiment of assembly 1 according to the invention. The assembly 1 is arranged in an aircraft having a cabin 4. The cabin 4 is pressurized thanks to a pressurizing device (not shown) which tends to maintain an absolute pressure within the cabin 4 above a minimum threshold of pressure.

The aircraft comprises a cockpit 2 having a wall to which the assembly 1 is fixed. In the embodiment illustrated, the assembly 1 is fixed at the top of the cabin 4 to a roof panel above the pilot's seats.

The assembly 1 comprises a respiratory mask 10 and a stowage device 50. The respiratory mask 10 is intended to be maintained by the stowage device 50 in a stowage position when it is not used and to be released from the stowage device 50 and placed in a use position on the face of the user, the user being in particular a pilot. The stowage device 50 comprises a base 20 and a platform 30.

The base 20 comprises a housing having an opening 29 and a bottom surface 21 opposite to the opening 29. The housing has a substantially parallelepiped shape and comprises a bottom wall 26, a first transverse wall 22, a second transverse wall 23, a first lateral wall 24 and a second lateral wall 25. The bottom wall 26 has the bottom surface 21 on an internal side and is in contact with the cockpit 2 to which it is secured on an external side. In variant, the housing could be received in a recess of the cockpit and the housing would advantageously comprise a flange.

The base 20 further comprises at least one door, a first door 27 and a second door 28 in the embodiment illustrated. The first door 27 and the second door 28 are movable between a closed position (shown in FIG. 1) in which the first door 27 and the second door 28 partially close the opening 29 and an opened position (shown in FIG. 3) in which the first door 27 and the second door 28 are away from the opening 29. The first door 27 is rotatably mounted on the first lateral wall 24 between the opened position and the closed position. The second door 28 is rotatably mounted on the second lateral wall 25 between the opened position and the closed position.

The respiratory mask 10 essentially comprises a face cover 12 and a harness 14. The face cover 12 has a peripheral edge defining a breathing cavity within which the user breathes in and out. The peripheral edge of the face cover 12 is suitable for applying on the face of the user. The respiratory mask 10 could also comprise a protective shield for protecting the eyes of the user from airborne elements, particularly smoke. In addition, the respiratory mask 10 comprises a rigid support 11. In the embodiment illustrated, the rigid support 11 serves as a housing containing a regulator. The regulator allows delivering breathing gas (having high rate of oxygen) on demand. The regulator is supplied with breathing gas via a supply hose.

The harness 14 comprises two elastic tubular devices. The elastic tubular devices are adapted to have their length extended when inflated. The elastic tubular devices form a first loop 15 and a second loop 16 adapted to extend around the head of a user in the use position. Each of the first loop 15 and the second loop 16 has a first end 15a, 16a connected to the rigid support 11 and a second end 15b, 16b connected to the rigid support 11. The first loop 15 and the second loop 16 are held apart by flexible spacer elements which extend generally vertically when the respiratory mask 10 is in the use position of the illustrated embodiment. In a variant, the first loop 15 and the second loop 16 could include a portion that is not part of the elastic tubular device and the flexible spacer elements could extend generally horizontally when the respiratory mask is in the use position.

The platform 30 comprises a main element 31, a first auxiliary element 32, a second auxiliary element 33, a third auxiliary element 34, a fourth auxiliary element 35 and a lever 36. The main element 31 is movable with respect to the base 20 between a retracted position (shown in FIG. 1 and in solid line in FIG. 2) and a protruding position (shown in FIG. 5 and in phantom line in FIG. 2). In the embodiment illustrated, the main element 31 is rigidly fixed to the lever 36 and the lever 36 is rotatable with respect to the base 20 around a rotation axis extending along a transverse direction Y. The lever 36 can be directly mounted on the base 20 or through the cockpit 2.

The movement of the platform 30 then describes a circular arc. According to this embodiment, the platform 30 pivots 45 to 135 degrees relative to the base 20 between the retracted position and the protruding position of the main element 31. More specifically, in the illustrated embodiment, the platform 30 rotates about 90 degrees relative to the base 20.

Figure 3:
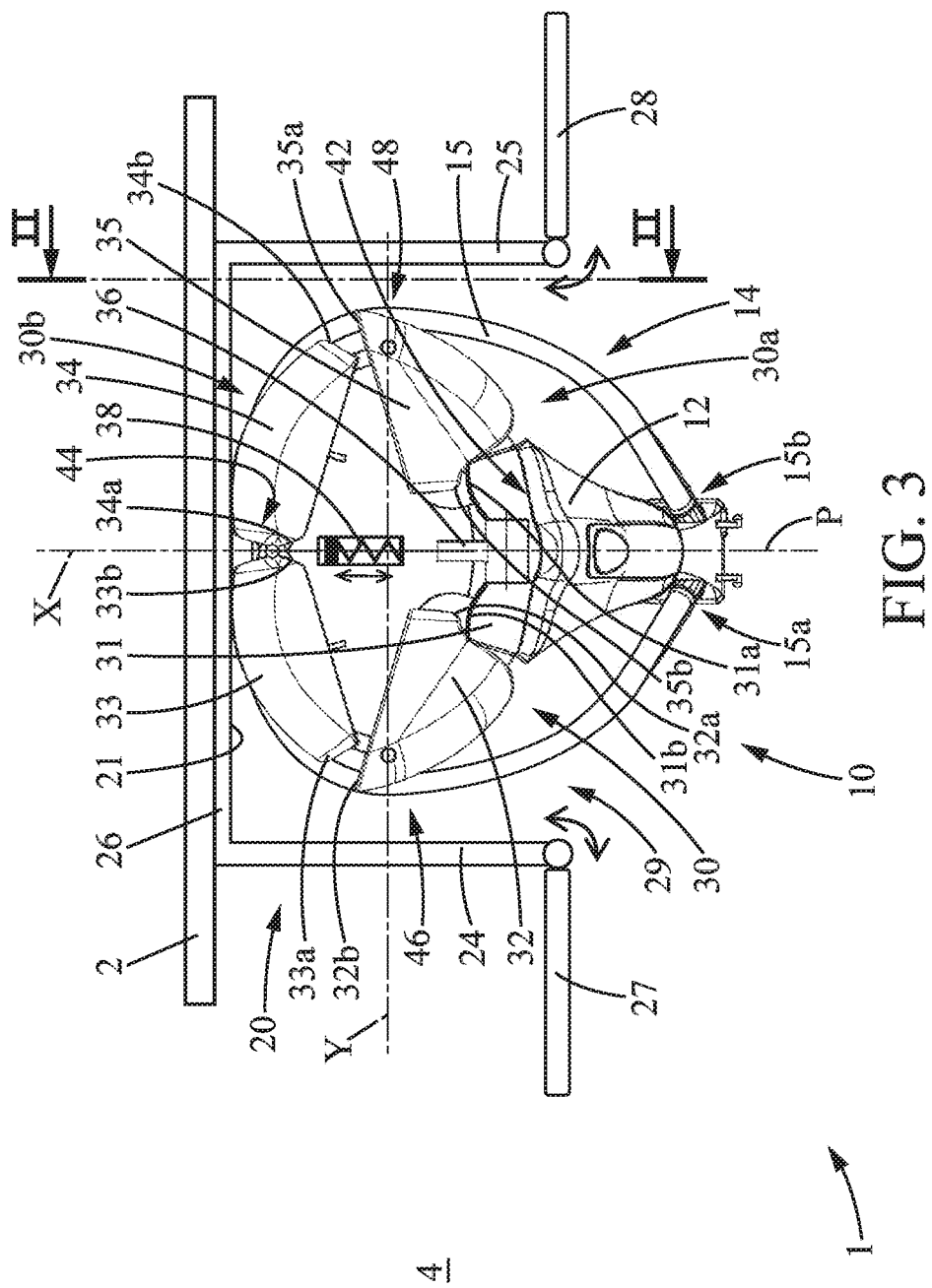

The platform 30 has a front side 30a and a back side 30b. The back side 30b is opposite to the front side 30a along a longitudinal direction X which is perpendicular to the transverse direction Y. As shown in FIG. 3, the platform 30 is symmetrical with respect to a plane of symmetry P. The plane of symmetry P is perpendicular to the transverse direction Y.

Figure 4:
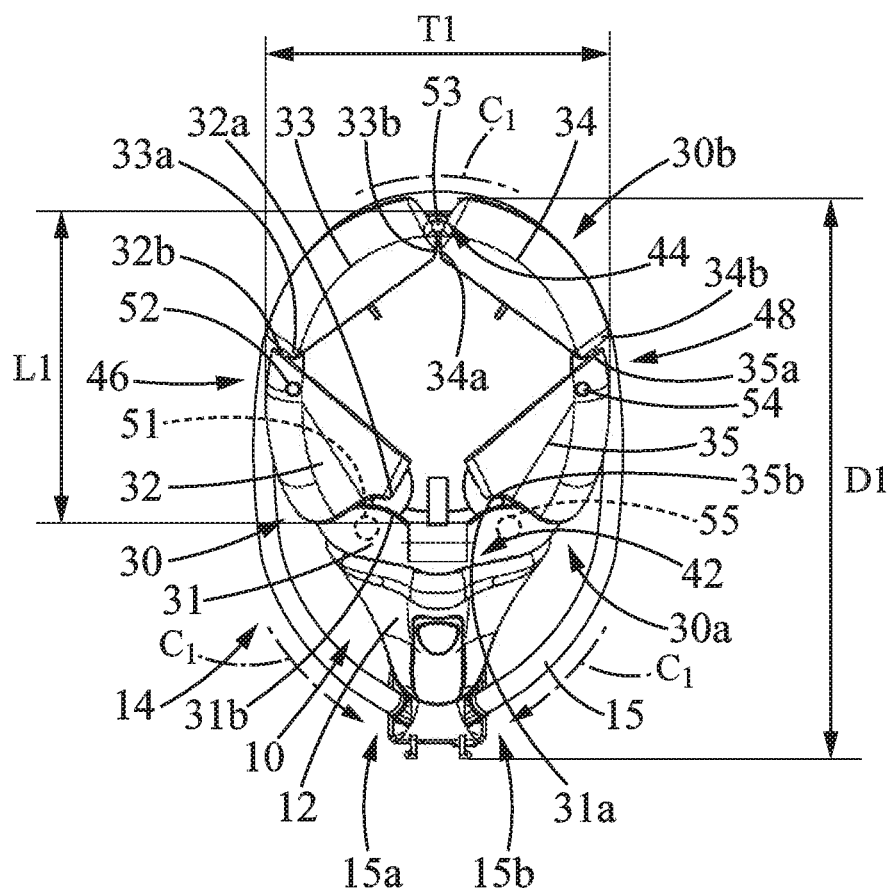

As shown in particular in FIG. 4, the platform 30 is adapted to receive the respiratory mask 10 in a stowage position where the first loop 15 and the second 16 of the harness 14 extend around the platform and contact a receiving surface 40 extending around the platform 30 for each of the first loop 15 and the second 16 of the harness 14. Each of the receiving surfaces 40 of the platform 30 comprises a first portion 42, a second portion 44, a third portion 46 and a fourth portion 48. The first portion 42 is on the front side 30a of the platform 30. The first portion 42 is contact with the face cover 12 when the respiratory mask 10 is in the stowage position. Each of the receiving surface 40 is preferably defined by a groove in order to maintain the first loop 15 and the second loop 16 of the harness along a direction Z which is perpendicular to the longitudinal direction X and to the transverse direction Y. In the embodiment illustrated, the first portion 42 of the receiving surface 40 is in the main element 31.

The second portion 44, the third portion 46 and the fourth portion 48 of the receiving surface 40 are in contact with the harness when the respiratory mask is in the stowage position, in order to hold the respiratory mask 10 on the platform 30. The second portion 44 of the receiving surface 40 is on the back side 30b of the platform 30. In the embodiment illustrated, the second portion 44 of the receiving surface 40 extends both on the second auxiliary element 33 and on the third auxiliary element 34. The third portion 46 extends on the first auxiliary element 32 and the fourth portion 48 extends on the fourth auxiliary element 35.

The main element 31, the first auxiliary element 32, the second auxiliary element 33, the third auxiliary element 34 and the fourth auxiliary element 35 are each rotatably mounted with respect to two other elements amongst them around two distant articulation axes extending along the direction Z. More accurately, as shown in particular in FIG. 5, the first auxiliary element 32 is rotatably connected to the main element 31 around a first articulation axis 51 extending along the direction Z, the second auxiliary element 33 is rotatably connected to the first auxiliary element 32 around a second articulation axis 52 extending along the direction Z, the third auxiliary element 34 is rotatably connected to the second auxiliary element 33 around a third articulation axis 53 extending along the direction Z, the fourth auxiliary element 35 is rotatably connected to the third auxiliary element 34 around a fourth articulation axis 54 extending along the direction Z and the main element 31 is rotatably connected to the fourth auxiliary element 35 around a fifth articulation axis 55 extending along the direction Z. Due to the possible movements between the main element 31, the first auxiliary element 32, the second auxiliary element 33, the third auxiliary element 34 and the fourth auxiliary element 35, the platform 30 has a flattened configuration (shown in FIG. 1 and in solid line in FIG. 2) and an expended configuration (shown in FIGS. 4 and 5, and in phantom line in FIG. 2).

During the movement of the platform 30 between the expended configuration and the flattened configuration (from the expended configuration to the flattened configuration and from the flattened configuration to the expended configuration), preferably the face cover 12 remains in contact with the first portion 42 of the receiving surface 40 and the harness 14 remains in contact with the second portion 44, the third portion 46 and the fourth portion 48 of the receiving surface 40 for the reasons explained below.

Figure 2:
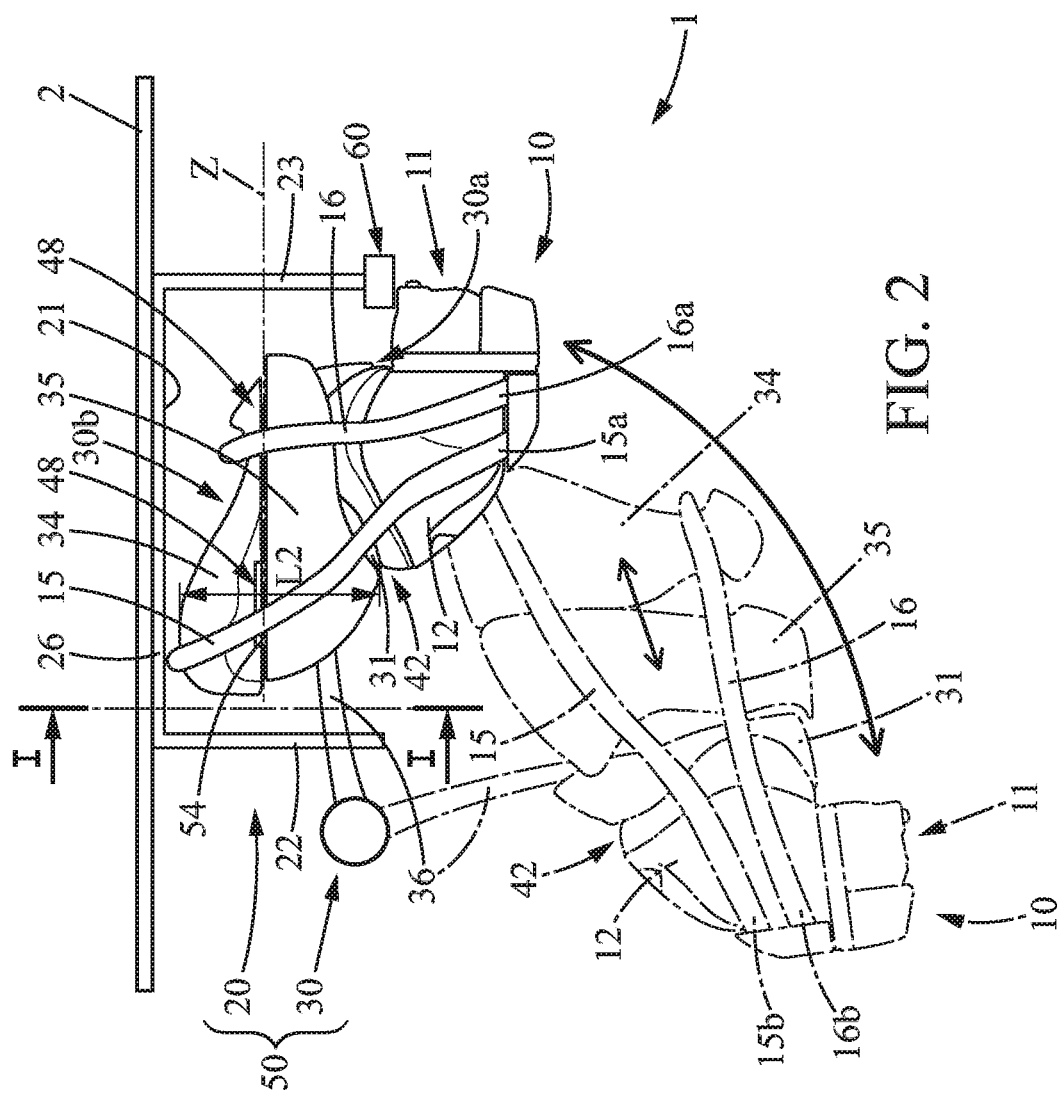

As shown in FIG. 4, in the expended configuration the second portion 44 of the receiving surface 40 is at a first longitudinal distance L1 from the first portion 42 of the receiving surface 40 along the longitudinal direction X. As shown in FIG. 2, in the flattened configuration the second portion 44 of the receiving surface 40 is at a second longitudinal distance L2 from the first portion 42 of the receiving surface 40 along the longitudinal direction X. The second longitudinal distance L2 is lower than 70% of the first longitudinal distance L1. The first longitudinal distance L1 and the second longitudinal distance are illustrated for the first loop 15, but in the illustrated embodiment the second longitudinal distance is also lower than 70% of the first longitudinal distance for the second loop 16.

As shown in FIG. 4, in the expended configuration, the fourth portion 48 of the receiving surface 40 is at a first transverse distance T1 from the third portion 46 of the receiving surface 40 along the transverse direction T. As shown in FIG. 1, in the flattened configuration the fourth portion 48 of the receiving surface 40 is at a second transverse distance T2 from the third portion 46 of the receiving surface 40 along the transverse direction T. The second lateral transverse distance T2 is at least 30% higher than the first transverse distance T1. As the transverse distance (along the transverse direction T) between the third portion 46 and the fourth portion 48 is increasing while the longitudinal distance (along the longitudinal direction X) between the first portion 42 and the second portion 44 is decreasing (and conversely), the circumference of the receiving surface 40 is quite steady (variation lower than 25%, preferably lower than 10%) which enable to keep the respiratory mask 10 safely maintained on the platform 30 when the platform 30 moves between the extended configuration and the flattened configuration.

As shown in FIG. 4, in the expended configuration of the platform the first loop 15 formed by the tubular device of the harness 14 has a first circumferential length C1 between the first end 15a and the second end 15b. As shown in FIG. 1, the first loop 15 formed by the tubular device of the harness 14 has a second circumferential length C2 in the flattened configuration between the first end 15a and the second end 15b. The second circumferential length C2 is higher than 75% of first circumferential length C1, preferably higher than 90% of first circumferential length C1. Of course, the second circumferential length C2 is lower than 125% of first circumferential length C1, preferably lower than 110% of first circumferential length C1. In the illustrated embodiment, the second circumferential length C2 is between 90% and 100% of the first circumferential length C1.

The second loop 16 has a second circumferential length in the flattened configuration (between the first end 16a and the second end 16b) which is between 75% and 125% (preferably between 90% and 110%) of a first circumferential length in the expended configuration (between the first end 16a and the second end 16b).

Moreover, as shown in FIG. 4, in the expended configuration of the platform 30, the respiratory mask 10 and the platform 30 have a first overall longitudinal dimension D1 along the longitudinal direction X. As shown in FIG. 1, in the flattened configuration of the platform 30, the respiratory mask 10 and the platform 30 have a second overall longitudinal dimension D2 along the longitudinal direction X. The second overall dimension D2 is lower than 75% of the first overall longitudinal dimension D1. Therefore, the flattened configuration of the platform enables to have the length (along the longitudinal direction X) of the first lateral wall 24 and the second lateral wall 25 reduced.

When the main element 31 is in the retracted position, the first door 27 and the second door 28 can be closed, the major portion of the respiratory mask 10 and the platform 30 are within into the base 20 whereas the depth of the housing along the longitudinal direction X is quite low.

As shown in FIG. 3, in the embodiment illustrated the platform 30 comprises an urging device including a jack. The jack comprises a spring 38, a compression spring in the illustrated embodiment, which urges the platform 30 in the expended configuration. The jack is connected at one end to the main element 31 and at the other end to the third articulation axis 53.

As shown in FIG. 4, in the expended configuration, an abutment portion 31b of the first auxiliary element 31 abuts against an abutment portion 32a of the second auxiliary element 32, an abutment portion 32b of the second auxiliary element 32 abuts against an abutment portion 33a of the third auxiliary element 33, an abutment portion 33b of the third auxiliary element 33 abuts against an abutment portion 34a of the fourth auxiliary element 34, an abutment portion 34b of the fourth auxiliary element 34 abuts against an abutment portion 35a of the fifth auxiliary element 34 and an abutment portion 35b of the fifth auxiliary element 35 abuts against an abutment portion 31a of the first auxiliary element 31. Therefore, the expended configuration of the platform 30 is well defined.

Some of these abutments are optional. For instance, in a first variant only the abutment of the abutment portion 33b of the second auxiliary element 33 against the abutment portion 34a of the third auxiliary element 34 could be kept. In a second variant, only the abutment of the abutment portion 31b of the main element 31 against the abutment portion 32a of the first auxiliary element 32 and the abutment of the abutment portion 35b of the fourth auxiliary element 35 against the abutment portion 31a of the main element 31 could be kept. In a third variant, only the abutment of the abutment portion 32b of the first auxiliary element 32 against the abutment portion 33a of the second auxiliary element 33 and the abutment of the abutment portion 34b of the third auxiliary element 34 against the abutment portion 35a of the fourth auxiliary element 35 could be kept. Other variants may be contemplated.

Preferably, the abutments are symmetrically arranged with respect to the plane of symmetry P.

In a variant, the urging device could include torsion springs acting on some of the articulation axis, to be substituted for the jack or in addition to the jack. For instance, the urging device could include a first torsion spring which urges the second auxiliary element 33 with respect to the first auxiliary element 32, so that the abutment portion 32b of the first auxiliary element 32 comes into abutment against the abutment portion 33a of the second auxiliary element 33 and a second torsion spring which urges the fourth auxiliary element 35 with respect to the third auxiliary element 34, so that the abutment portion 34b of the third auxiliary element 34 comes into abutment against the abutment portion 35a of the fourth auxiliary element 35.

As shown in FIGS. 1 to 3, when the main element 31 is moved from the protruding position to the retracted position, the second auxiliary element 33 and the third auxiliary element 34 abuts against the bottom surface 21 and the platform 30 consequently moves from the expended configuration to the flattened configuration.

In order to hold the main element 31 in the retracted position a retaining device 60 operating by magnetic attraction is provided. The retaining device 60 preferably comprises a magnetizable element and a retaining element, one being fixed to the base 20 the other being fixed to the rigid support 11 of the respiratory mask 15 (in variant it could be fixed directly to the platform 15) in the illustrated embodiment. The magnetizable element and the retaining element are in immediate proximity to one another in the retracted position of the main element. The electromagnet can be connected to the avionics and control the release of the main element 11 according to navigational conditions. In a variant, the electromagnet could be replaced by a simple magnet, even if it is not a preferred embodiment. In another variant, instead of being of magnetic type, the retaining device could be of abutment type and could comprise a hook releasably cooperating with a flange. A more detailed description of such a retaining device and other convenient retaining devices can be found in WO2017/055764A1.

In the illustrated embodiment, the retaining device 60 retains the rigid portion 11 of the respiratory mask with respect to the base 20. In variant, the retaining 60 could act on the lever 36, in order to maintain the main element 31 in the retracted position, and the platform 30 in the flattened configuration.

A method for providing the respiratory mask 10 and a method for stowing the respiratory mask 10 according to the invention will now be described.

When the respiratory mask 10 is maintained on the platform 30 in the stowage position, the main element 31 is in the retracted position and the platform 30 is in the flattened configuration as shown in FIG. 1 and the surrounding conditions so require (for instance in case of failure of the pressurizing device), the retaining device 60 is operated to release the main element 31 of the platform 30. In a variant, the user may grasp the rigid portion 11 of the respiratory mask and pulls the respiratory mask 10 to release the main element 31. Gravity (and optionally an urging device, a pneumatic device, an electrical motor or the like) causes the main element 31 to pivot about the rotation axis from the retracted position to the protruding position. The first door 27 and the second door 28 are driven by the movement of the respiratory mask 10 which pushes the first door 27 and the second door 28. The opening of the first door 27 and the second door 28 preferably causes the regulator of the respiratory mask to be supplied in breathing gas. While the main element 31 is pivoting about the rotation axis, the platform 30 is moving from the flattened configuration to the expended configuration as the platform is not abutting against the bottom surface 21 anymore, as shown in particular in FIG. 2.

Figure 5:
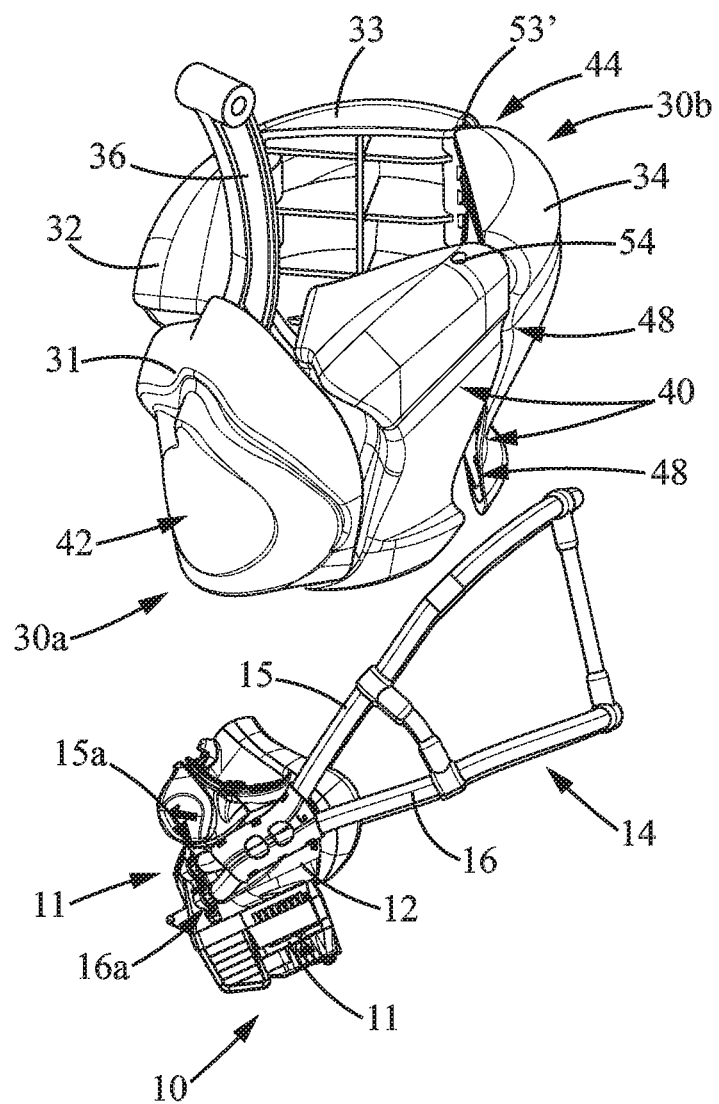

In a second step, as shown in particular in FIG. 5, the main element 31 being in the protruding position and the platform 30 being in the expended configuration, the respiratory mask 10 is removed from the platform 30. To remove the respiratory mask 10 from the platform 30, the user grasps the rigid support 11 of the respiratory mask and causes the harness 14 to be inflated. The harness 14 is thus in the deployed position. Then, the user pulls downwards on the respiratory mask 10. The respiratory mask 10 is thus freed from the platform 30; the user can then don it and deflate the harness in order to maintain the face cover 12 against his face thanks to the harness 14. The user can send the platform 30 back into the housing 17, by rotating the main element 31 toward the retracted position.

In order to stow the mask, the user brings the main element 31 in the protruding position, grasps the respiratory mask 10 by the rigid support 1 and inflates the harness. The length of the harness 14 is therefore increased; the loops 15, 16 are larger, so that the user can place the harness 14 around the platform 30 and the face cover 12 facing the first portion 42 of the receiving surface 40. Then, the user deflates the harness 14. Deflation of the harness 14 thus permits the harness 14 to retract around the platform 30 and contact the receiving surface 40, in particular the second portion 44, the third portion 46 and the fourth portion 48 of the receiving surface 40, so that the face cover 12 is pressed against the first portion 42 of the receiving surface, as shown in phantom line in FIG. 2. The grooves of the receiving surface 40 serve to guide the harness 14 as it retracts. However, such grooves are not essential to the invention. Next, the user pushes the main element 31 in order to place it into the retracted position. When the platform 30 contacts the bottom surface 21, the platform 30 moves from the expended configuration to the flattened configuration while the main element 31 moves to the retracted position. The main element 31 is maintained in the retracted position by the retaining device 60. The first door 27 and the second door 28 can then be closed near the respiratory mask 10, while maintaining a portion of the rigid portion 11 outside the housing for enabling the user to easily grasp it.

The second embodiment illustrated in FIGS. 6 to 9 mainly differs from the first embodiment illustrated in FIGS. 1 to 5 on three separate aspects.

According to a first aspect, the shape of the first auxiliary element 42, the second auxiliary element 44, the third auxiliary element 46 and the fourth auxiliary element 48 is modified as well as the position of the first articulation axis 51, the second articulation axis 52, the third articulation axis 53, the fourth articulation axis 54 and the fifth articulation axis 55, so that in the flattened configuration (shown in FIGS. 6 and 7), the third portion 46 of the receiving surface 40 is between the first portion 42 of the receiving surface 40 and the first end 15a, 16a of the harness 14 for each loop 15, 16 and the fourth portion 48 of the receiving surface 40 is between the first portion 42 of the receiving surface 40 and the second end 15b, 16b of the harness 14 for each loop 15, 16.

Therefore, in the second embodiment, the second longitudinal distance L2 (between the first portion 42 and the second portion 44 of the receiving surface 40, along the longitudinal direction X, in the flattened configuration) is lower than 50% of the first longitudinal distance L1 (between the first portion 42 and the second portion 44 of the receiving surface 40, along the longitudinal direction X, in the expended configuration) for each of the first loop 15 and the second loop 16, the second lateral transverse distance T2 (between the third portion 46 and the fourth portion 48 of the receiving surface 40, along the transverse direction Y, in the flattened configuration) is at least 40% higher than the first transverse distance T1 (between the third portion 46 and the fourth portion 48 of the receiving surface 40, along the transverse direction Y, in the expended configuration) and the second overall dimension D2 (along the longitudinal direction X, in the flattened configuration) is lower than 65% of the first overall longitudinal dimension D1 (along the longitudinal direction X, in the expended configuration).

Figure 7:
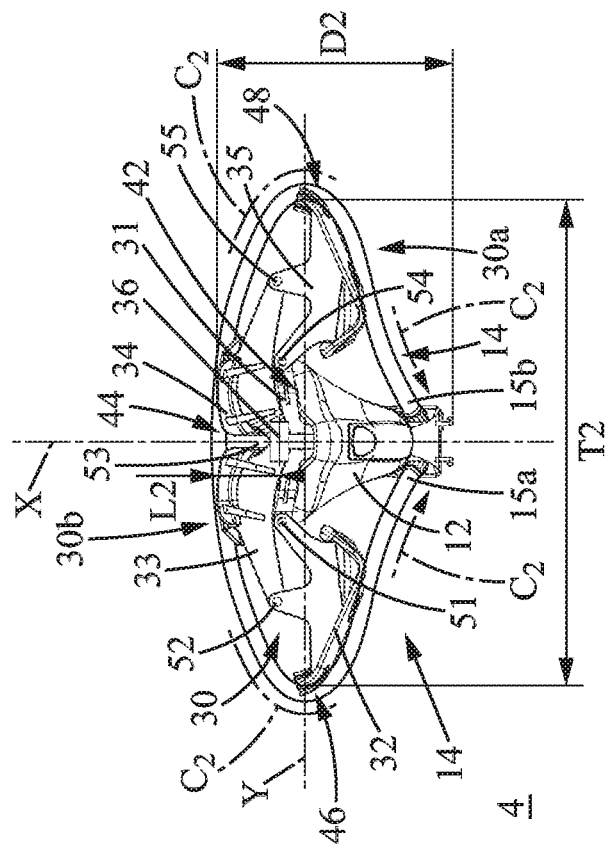
Figure 6:
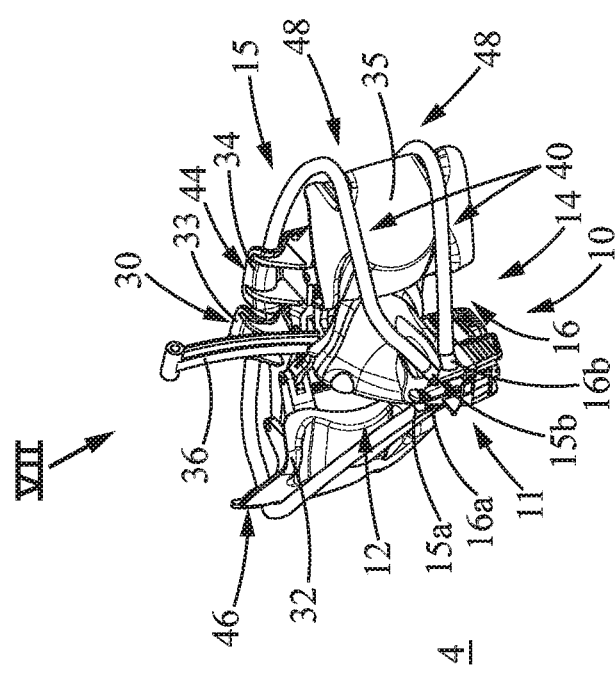
Figure 9:
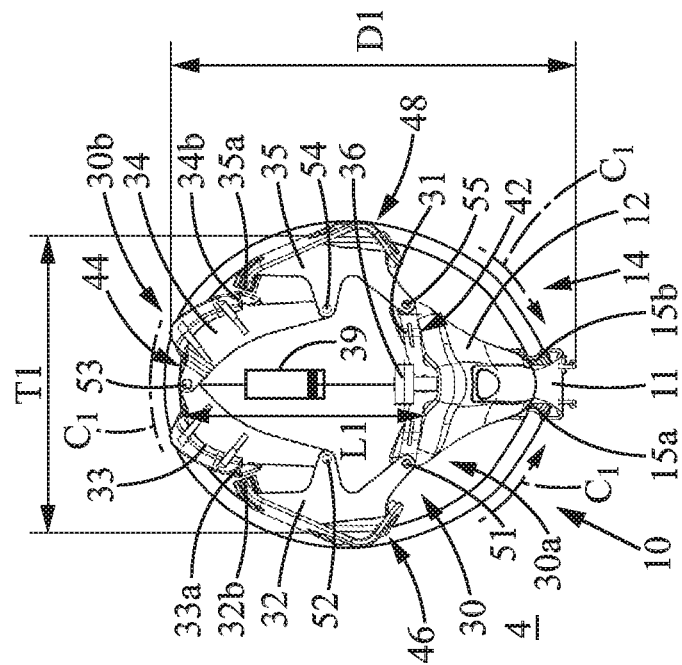
Figure 8:
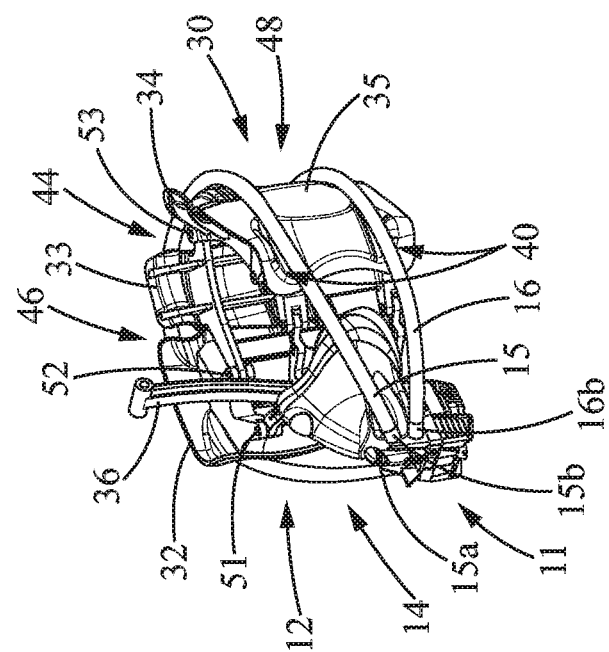

As shown in FIG. 7 and FIG. 9, in the second embodiment, in the stowage position of the respiratory mask 15, the second circumferential length C2 (of the first loop 15) between the first end 15a and the second end 15b, in the flattened configuration of the platform 30 is between 75% (preferably higher than 90%) and 125% (preferably lower than 110%) of the first circumferential length C1. The variation of the circumferential length of the second loop 16 in the stowage position of the respiratory mask 15 between the expanded configuration and the flattened configuration of the platform 30 is also lower than 25% (preferably lower than 10%) of the first circumferential length in the expanded configuration.

The second loop 16 has a second circumferential length in the flattened configuration (between the first end 16a and the second end 16b) which is between 75% and 125% (preferably between 90% and 110%) of a first circumferential length in the expended configuration (between the first end 16a and the second end 16b).

According to a second aspect, in the expanded configuration of platform 30, only the abutment portion 32b of first auxiliary element 32 comes into abutment against the abutment portion 33a of the second auxiliary element 33 and the abutment portion 34b of third auxiliary element 34 comes into abutment against the abutment portion 35a of the fourth auxiliary element 35 which is sufficient for having a constant expanded configuration of platform 30, the platform 30 being urged in the expanded configuration by any one of possible urging device (not shown in the figures) mentioned in connection with the first embodiment.

According to a third aspect, the spring 38 is replaced by a pneumatic jack 39. In case, the surrounding conditions so require (for instance in case of failure of the pressurizing device, smoke or the like), the pneumatic jack 39 is operated to move the platform 30 from the flattened configuration to the release configuration. As the platform abuts against the abutment surface 21, the rigid support 11 and the face cover 12 moves along the longitudinal direction X which causes the opening of the first door 27 and the second door 28. Moreover, the rigid portion 11 of the respiratory mask 14 is moved away from the retaining device 60, so that it is not retained by the retaining device 60 which is of magnetic type and the main element 31 moves then by gravity to the protruding position.

Of course, the invention is not limited to the illustrated embodiments provided for indicative and non-limiting purposes. Thus, although such is not preferred, the platform could be movable in translation relative to the base. In addition, the rotation axis of the lever 36 could be movable in translation relative to the base 20.

In addition, the respiratory mask 10 could comprise a protective shield separate from the face cover 12, the protective shield being in particular releasable relative to the face cover 12. Alternatively, the protective shield could be fixed relative to the face cover 12. According to another variant, the shield could be integrated into the face cover 12, forming a mask usually referred to as "full face", the respiratory cavity within which the user breathes in and out also extending around the user's eyes.

Otherwise, the movement of the platform between the expanded configuration and the flattened configuration could be linked to the movement of the main element between the protruding position and the retracted position by a mechanical joint, in particular a rigid link.

The invention claimed is:

1. Assembly intended in particular to be arranged in a cockpit of an aircraft having a pressurized cabin in order to supply a breathing gas to a crew member, said assembly comprising a respiratory mask and a stowage device, wherein:
   the respiratory mask has a face cover and a harness,
   the stowage device comprises a base and a platform,
   the platform has a front side and a back side,
   the platform has a receiving surface extending around the platform, the receiving surface has a first portion on the front side and a second portion on the back side,
   the platform is adapted to receive the respiratory mask in a stowage position where the harness forms a loop extending around the platform and contacting the receiving surface, the face cover contacting the first portion of the receiving surface and the harness contacting the second portion of the receiving surface, so as to hold the respiratory mask on the platform,
   the platform comprises a main element, the main element being movable relative to the base (between a retracted position and a protruding position,
   the platform further comprises auxiliary elements, the auxiliary elements being movable with respect to the main element between a flattened configuration and an expanded configuration of the platform,
   in the expanded configuration of the platform, the second portion of the receiving surface is at a first longitudinal distance from the first portion of the receiving surface in a longitudinal direction, and
   in the flattened configuration of the platform, the second portion of the receiving surface is at a second longitudinal distance from the first portion of the receiving surface, the second longitudinal distance being lower than the first longitudinal distance.

2. Assembly according to claim 1 wherein:
   the receiving surface further comprises a third portion and a fourth portion,
   the harness contacts the third portion and the fourth portion of the receiving surface when the respiratory mask is in the stowage position and the platform is in the flattened configuration,
   the fourth portion of the receiving surface is at a first transverse distance from the third portion of the receiving surface in a transverse direction in the expanded configuration of the platform, and
   the fourth portion of the receiving surface is at a second lateral transverse distance from the third portion of the receiving surface in the flattened configuration of the platform, the second transverse distance being higher than the first transverse distance.

3. Assembly according to claim 2 wherein the second lateral transverse distance is at least 30% higher than the first lateral transverse distance.

4. Assembly according to claim 2 wherein the second lateral transverse distance is at least 40% higher than the first lateral transverse distance.

5. Assembly according to claim 2 wherein:
   the respiratory mask has a rigid support supporting the face cover,
   the harness has a first end connected to the rigid support and a second end connected to the rigid support,
   in the flattened configuration, along the longitudinal direction, the third portion is between the first end of the harness and the first portion of the receiving surface, and
   in the flattened configuration, along the longitudinal direction, the fourth portion is between the second end of the harness and the first portion of the receiving surface.

6. Assembly according to claim 1 wherein:
   the loop of the harness comprises at least one elastic tubular portion and has a first circumferential length in the expanded configuration of the platform and a second circumferential length in the flattened configuration of the platform, and
   the second circumferential length differs from the first circumferential length variation by less than 25%.

7. Assembly according to claim 1 wherein:
   the loop of the harness comprises at least one elastic tubular portion and has a first circumferential length in the expanded configuration of the platform and a second circumferential length in the flattened configuration of the platform, and
   the second circumferential length differs from the first circumferential length variation by less than 10%.

8. Assembly according to claim 1 wherein the platform is urged into the expanded configuration.

9. Assembly according to claim 8 wherein when the main element is in the retracted position, the platform abuts against an abutment surface of the base maintaining the platform in the flattened configuration.

10. Assembly according to claim 9 wherein:
at least one spring urges the platform into the expanded configuration, and
the abutment of the platform against the abutment surface of the base maintains the platform in the flattened configuration when the main element is in the retracted position.

11. Assembly according to claim 1 wherein the main element includes the first portion of the receiving surface.

12. Assembly according to claim 1 wherein the main element comprises a lever rotatably mounted on the base.

13. Assembly according to claim 1 wherein the platform comprises:
a first auxiliary element rotatably connected to the main element,
a second auxiliary element rotatably connected to the first auxiliary element,
a third auxiliary element rotatably connected to the second auxiliary element, and
a fourth auxiliary element rotatably connected to the third auxiliary element and to the main element.

14. Assembly according to claim 1 wherein the second longitudinal distance is lower than 70% of the first longitudinal distance.

15. Assembly according to claim 1 wherein the second longitudinal distance is lower than 50% of the first longitudinal distance.

16. Assembly according to claim 1 wherein:
the respiratory mask and the platform have a first overall longitudinal dimension along the longitudinal direction when the platform is in the expanded configuration,
the respiratory mask and the platform have a second overall longitudinal dimension along the longitudinal direction when the platform is in the flattened configuration, and
the second overall longitudinal dimension is lower than 75% of the first overall longitudinal dimension.

17. Assembly according to claim 1 wherein:
the respiratory mask and the platform have a first overall longitudinal dimension along the longitudinal direction when the platform is in the expanded configuration,
the respiratory mask and the platform have a second overall longitudinal dimension along the longitudinal direction when the platform is in the flattened configuration, and
the second overall longitudinal dimension is lower than 65%, of the first overall longitudinal dimension.

18. Method for stowing a respiratory mask wherein an assembly comprising the respiratory mask is intended to be arranged in particular in a cockpit of an aircraft having a pressurized cabin in order to supply breathing gas to a crew member, the respiratory mask having a face cover and a harness, said assembly further comprising a stowage device, the stowage device comprising a base and a platform, the platform comprises a main element movable relative to the base between a retracted position and a protruding position, the platform has a flattened configuration and an expanded configuration, wherein said method comprises:

a) placing the main element (in the protruding position and the platform in the expanded configuration, the platform having a first longitudinal dimension along a longitudinal direction in the expanded configuration, b) bringing the respiratory mask to a stowage position where the harness forms a loop extending around the platform so as to hold the respiratory mask on the platform, c) moving the main element into the retracted position and placing the platform in the flattened configuration, the platform having a second longitudinal dimension along the longitudinal direction in the flattened configuration, the second longitudinal dimension being smaller than the first longitudinal dimension.

19. Method for providing a respiratory mask wherein an assembly comprising the respiratory mask is intended to be arranged in particular in a cockpit of an aircraft having a pressurized cabin in order to supply breathing gas to a crew member, the respiratory mask having a face cover and a harness, said assembly further comprising a stowage device, the stowage device comprising a base and a platform, the platform comprises a main element movable relative to the base between a retracted position and a protruding position, the platform has a flattened configuration and an expanded configuration, wherein said method comprises:

a) placing the main element in the retracted position, placing the platform in the flattened configuration and placing the respiratory mask in a stowage position where the harness forms a loop extending around the platform so as to hold the respiratory mask on the platform, the platform having a first longitudinal dimension along a longitudinal direction in the expanded configuration and a second longitudinal dimension along the longitudinal direction in the flattened configuration, the second longitudinal dimension being smaller than the first longitudinal dimension, b) moving the main element into the protruding position and placing the platform in the expanded configuration, and c) removing the respiratory mask from the platform.

* * * * *